(12) United States Patent
Boughorbel et al.

(10) Patent No.: US 8,581,189 B2
(45) Date of Patent: Nov. 12, 2013

(54) CHARGED PARTICLE MICROSCOPY IMAGING METHOD

(75) Inventors: Faysal Boughorbel, Eindhoven (NL); Eric Gerardus Theodoor Bosch, Eindhoven (NL); Cornelis Sander Kooijman, Veldhoven (NL); Berend Helmerus Lich, Weert (NL); Alan Frank de Jong, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/572,206

(22) Filed: Aug. 10, 2012

(65) Prior Publication Data
US 2013/0037714 A1 Feb. 14, 2013

Related U.S. Application Data

(60) Provisional application No. 61/522,177, filed on Aug. 10, 2011.

(30) Foreign Application Priority Data

Aug. 10, 2011 (EP) .................................... 11177091

(51) Int. Cl.
*H01J 37/26* (2006.01)
(52) U.S. Cl.
USPC ............ 250/307; 250/306; 250/310; 250/311
(58) Field of Classification Search
USPC .................................. 250/306, 307, 310, 311
See application file for complete search history.

(56) References Cited

U.S. PATENT DOCUMENTS

| 5,412,210 | A | 5/1995 | Todokoro et al. | |
|---|---|---|---|---|
| 8,232,523 | B2 * | 7/2012 | Boughorbel et al. | 250/307 |
| 8,461,527 | B2 * | 6/2013 | Nakahira et al. | 250/310 |
| 2003/0132382 | A1 * | 7/2003 | Sogard | 250/311 |
| 2009/0078868 | A1 | 3/2009 | de Jonge | |
| 2011/0187847 | A1 * | 8/2011 | Bai et al. | 348/80 |
| 2011/0266440 | A1 * | 11/2011 | Boughorbel et al. | 250/310 |
| 2012/0049060 | A1 | 3/2012 | Luecken et al. | |
| 2012/0097848 | A1 * | 4/2012 | Lifshin et al. | 250/307 |
| 2012/0292503 | A1 | 11/2012 | Phifer, Jr. et al. | |
| 2013/0037715 | A1 * | 2/2013 | Boughorbel et al. | 250/307 |

OTHER PUBLICATIONS

Alimov, V. KH., et al., 'Depth distribution of deuterium in single- and polycrystalline tungsten up to depths of serveral micrometers,' Journal of Nuclear Materials, Mar. 1, 2005, pp. 619-623, vol. 337-339.

(Continued)

*Primary Examiner* — Michael Logie
(74) *Attorney, Agent, or Firm* — Scheinberg & Associates, PC; Michael O. Scheinberg

(57) ABSTRACT

A charged-particle microscopy includes irradiating a sample in measurement sessions, each having an associated beam parameter (P) value detecting radiation emitted during each measurement session, associating a measurand (M) with each measurement session, thus providing a data set (S) of data pairs $\{P_n, M_n\}$, wherein an integer in the range of $1 \leq n \leq N$, and processing the set (S) by: defining a Point Spread Function (K) having a kernel value $K_n$ for each value n; defining a spatial variable (V); defining an imaging quantity (Q) having fore each value of n a value $Q_n$ that is a three-dimensional convolution of $K_n$ and V, such that $Q_n = K_n * V$; for each value of n, determining a minimum divergence min $D(M_n \| K_n * V)$ between $M_n$ and $Q_n$, solving V while applying constraints on the values $K_n$.

20 Claims, 4 Drawing Sheets

(56) References Cited

OTHER PUBLICATIONS

Ditsman, S.A., et al., 'Stereomicrotomography as a New Method of Scanning Electron Microscopy Investigation of Three-Dimensional Microstructures,' Journal of Surface Investigation, Jan. 1, 2001, pp. 1841-1844, vol. 16, No. 12.
'Site-Specific Cross-Sectioning,' Introduction to Focused Ion Beams, Jan. 1, 2004, pp. 250-255.
Niedrig, H., et al., 'Information depth and spatial resolution in BSE microtomography in SEM,' Nuclear Instruments and Methods in Physics Research B, Aug. 1, 1998, pp. 523-534, vol. 142, No. 4.
Pezzotti, Giuseppe, et al., 'Spatially resolved residual stress assessments of GaN film on sapphire substrate by cathodoluminescence piezospectroscopy,' Journal of Applied Physics, Jul. 21, 2008, pp. 23514-23514, vol. 104, No. 2.
Sato, Kazuhisa, et al., 'Three-dimensional shapes and distribution of FePd nanoparticles observed by electron tomography using high-angle annular dark-field scanning transmission electron microscopy,' Journal of Applied Physics, Jan. 20, 2010, pp. 24304-24304, vol. 107, No. 2.
Sokolov, V.N., et al., 'Analysis of SEM stereoscopic images,' Bulletin of the Russian Academy of Sciences: Physics, 1996, pp. 208-215, vol. 60, No. 2.
Van Den Broek, W., et al., 'A model based reconstruction technique for depth sectioning with scanning transmission electron microscopy,' Ultramicroscopy, Apr. 1, 2010, vol. 110, No. 5.
Zhu, Wenliang, et al., 'Spatially resolved crack-tip stress analysis in semiconductor by cathodoluminesence piezospectroscopy,' Journal of Applied Physics, May 30, 2007, pp. 8-11, vol. 101, No. 10.
Alimov, V.KH., et al., "Depth distribution of deuterium in single- and polycrystalline tungsten up to depths of several micrometers," Journal of Nuclear Material, Mar. 2005, pp. 619-623, vol. 337-339.
Cichocki, Andrzej, et al., "Families of Alpha-Beta- and Gamma-Divergences: Flexible and Robust Measures of Similarities," Entropy, 2010, pp. 1532-1568, vol. 12.
Cichocki, Andrzej, et al., "Generalized Alpha-Beta Divergences and Their Application to Robust Nonnegative Matrix Factorization," Entropy, 2011, pp. 134-170, vol. 13.
Lanteri, Henri, et al., "Penalized maximum likelihood image restoration with positivity constraints: multiplicative algorithms." Inverse Problems, 2002, pp. 1397-1419, vol. 18.
Pezzotti, Giuseppe, et al., "Spatially resolved residual stress assessments of GaN film on sapphire substrate by cathodoluminescence piezospectroscopy," Journal of Applied Physics, Jul. 2008, 12 pgs, vol. 104, No. 2.
Press, William, et al., "Numerical Recipes in C: The Art of Scientific Computing," 1992, pp. 418-479, 2 ed., Cambridge University Press.
Richardson, William, Hadley, "Bayesian-Based Iterative Method of Image Restoration," Journal of the Optical Society of America, Jan. 1972, pp. 55-59, vol. 62, No. 1.
Shepp, L.A., et al., "Maximum Likelihood Reconstruction for Emission Tomography," IEEE Transaction on Medical Imaging, Oct. 1982, pp. 113-122, vol. MI-1, No. 2.
Unknown, "Bhattacharyya distance." Website, http://en.wikipedia.org/wiki/Bhattacharyya_distance, Publication date unknown, Retrieved Nov. 9, 2012, 3 Pages.
Unknown, "Bregman divergence." Website, http://en.wikipedia.org/wiki/Bregman_divergence, Publication date unknown, Retrieved Nov. 9, 2012, 4 Pages.
Unknown, "Cramer-Rao bound." Website, http://en.wikipedia.org/wiki/Cramer-Roa_bound, Publication date unknown, Retrieved Nov. 9, 2012, 9 Pages.
Unknown, "Expectation-maximization algorithm." Website, http://en.wikipedia.org/wiki/Expectation-maximization_algorithm, Publication date unknown, Retrieved Nov. 9, 2012, 12 Pages.
Unknown, "F-divergence." Website, http://en.wikipedia.org/wiki/F-divergence, Publication date unknown, Retrieved Nov. 9, 2012, 3 Pages.
Unknown, "Finite element method." Website, http://en.wikipedia.org/wiki/Finite_element_method, Publication date unknown, Retrieved Nov. 9, 2012, 14 Pages.
Unknown, "Kullback-Leibler divergence." Website, http://en.wikipedia.org/wiki/Kullback-Leibler_divergence, Publication date unknown, Retrieved Nov. 9, 2012, 14 Pages.
Unknown, "Least squares." Website, http://en.wikipedia.org/wiki/Least_squares, Publication date unknown, Retrieved Nov. 9, 2012, 11 Pages.
Unknown, "Mathematical optimization." Website, http://en.wikipedia.org/wiki/Mathematical_optimization, Publication date unknown, Retrieved Nov. 9, 2012, 15 Pages.
Unknown, "Monte Carlo method." Website, http://en.wikipedia.org/wiki/Monte_Carlo_method, Publication date unknown, Retrieved Nov. 9, 2012, 14 Pages.
Wenliang, Zhu, et al., 'Spatially resolved crack-tip stress analysis in semiconductor by cathodoluminescence piezospectroscopy,' Journal of Applied Physics, May 30, 2007, pgs. vol. 101, No. 10.
Dreomova, N.N., et al., 'Characterization of multilayer microstructures and surface relief using backscattered electrons in a scanning electron microscope,' Bulletin of the Russian Academy of Sciences—Physics, Jan. 1, 1993, pp. 1305-1310, vol. 57, No. 8.
Gostev, A.V., et al., 'Information depth of the backreflected electron mode in scanning electron microscopy,' Bulletin of the Russian Academy of Sciences—Physics, Jan. 1, 1998, pp. 475-480, vol. 62, No. 3.
Donolato, C., 'An Analytical Model of SEM and STEM Charge Collection Images of Dislocations in Thin Semiconductor Layers: I. Minority carrier generation, diffusion, and collection' Physica Status Solidi (A), Jun. 16, 1981, pp. 649-658, vol. 65, No. 2.
Dong, Wende, et al., 'A piecewise local regularized Richardson-Lucy algorithm for remote sensing image deconvolution,' Optics & Laser Technology, Dec. 30, 2010, pp. 926-933, vol. 43.
Gordon, Richard, et al., 'Algebraic Reconstruction Techniques (ART) for Three-dimensional Electron Microscopy and X-Ray Photography,' J. theor. Biol., 1970, pp. 471-481, vol. 29.
Hoyer, Patrik O., 'Non-negative Matrix Factorization with Sparseness Constraints,' Journal of Machine Learning Research, Nov. 2004, pp. 1457-1469, vol. 5.
McNally, James, G. et al., 'Three-Dimensional Imaging by Deconvolution Microscopy,' Methods, 1999, pp. 373-385, vol. 19.
Lanteri, Henri, et al., 'Penalized maximum likelihood image restoration with positivity constraints: multiplicative algorithms,' Inverse Problems, 2002, pp. 1397-1419, vol. 18.
Starck, J.L., et al., 'Deconvolution in Astronomy: A Review,' Publications of the Astronomical Society of the Pacific, Oct. 2002, pp. 1051-1069, vol. 114.
Strong, David, et al., 'Edge-preserving and scale-dependent properties of total variation regularization,' Inverse Problems, 2003, pp. S165-S187, vol. 19.
Tikhonov, A.N., 'On the stability of inverse problems,' Compte Rendus (Doklady) de l'Academie des Sciences de l'Urss, 6 pgs, 1943, vol. 39, No. 5.

\* cited by examiner

CHARGED PARTICLE MICROSCOPY IMAGING METHOD

This application claims priority from U.S. Provisional Patent Application 61/522,177, filed Aug. 10, 2011, which is hereby incorporated by reference.

The invention relates to a method of investigating a sample using charged-particle microscopy, comprising the following steps:

Irradiating a surface of the sample using a probing beam of charged particles in a plurality (N) of measurement sessions, each measurement session having an associated beam parameter (P) value that is chosen from a range of such values and that differs between measurement sessions;

Detecting stimulated radiation emitted by the sample during each measurement session, associating a measurand (M) therewith and noting the value of this measurand for each measurement session, thus allowing compilation of a data set (S) of data pairs $\{P_n, M_n\}$, where n is an integer in the range $1 \leq n \leq N$.

The invention also relates to an apparatus for performing such a method.

A method as set forth in the opening paragraph is known from U.S. Pat. No. 5,412,210, and makes use of the insight that changing the primary beam energy in a Scanning Electron Microscope (SEM) leads to deeper penetration inside the sample being investigated. In principle, such an approach can be used to generate quasi-tomograms of regions of interest in the sample. Up to now, attempts to exploit this approach have involved acquiring two or more images with increasing primary beam energy, adjusting contrast between the images, and then subtracting lower-energy images from higher-energy images to reveal submerged layers in the sample.

A drawback of such known approaches is that said inter-image contrast adjustment (which is a key step) can only be performed using knowledge about the composition and geometry of the sample. Consequently, prior applications of this technique have tended to limit themselves to wafer defect inspection and other semiconductor applications, in which there is generally good a priori knowledge of the sample's (default) composition and geometry. Since the required compositional and geometrical information is typically not available for biological samples, the known technique has not yet been successfully applied to investigations in the life sciences.

A method as set forth in the opening paragraph is also known from co-pending European patent application EP-A 11163992 (FNL1015), which has a common inventor with the current invention. In said application, a sample is probed by a SEM electron beam at a range of different beam parameters, and the intensity of backscattered (BS) electrons emanating from the sample is measured. The data thus obtained are subsequently automatically processed, by using second-order and higher-order statistics from a range of Blind Source Separation techniques to deconvolute signals coming from different layer depths (z-levels) within the sample. In this way, one is able to calculate a set of images of the sample for a corresponding set of said different layer depths.

A drawback of the approach in the previous paragraph is that it assumes that the region of interaction of the probing electron beam with the sample is basically only longitudinal in form (i.e. essentially one-dimensional, along a z-axis), with essentially no lateral spread (i.e. no higher-dimensional components, along x/y axes). Although such a simplification can correlate relatively closely to reality in certain situations, e.g. when using a probing electron beam with relatively low landing energies, it can deviate more significantly from reality in other situations, e.g. when employing relatively high landing energies, or using specifically shaped beams/sources, or probing the sample at non-perpendicular incidence angles, or detecting X-rays emanating from the sample instead of BS electrons, or combinations of such scenarios. In instances such as these, the accuracy/usefulness of the calculated set of images will generally be inadequate.

It is an object of the present invention to address the issues set forth above. More specifically, it is an object of the present invention to provide a charged-particle microscopy imaging method that lends itself to application with samples comprising unknown composition/geometry, and that allows automatic deconvolution of measured data and automatic generation of sub-surface imagery. In particular, it is an object of the present invention that such generated imagery should be three-dimensional, producing reliable imaging results even in situations where the region of interaction of a probing charged-particle beam with a sample cannot be simplified to a (quasi-) one-dimensional form.

These and other objects are obtained in a method as set forth in the opening paragraph, characterized in that a mathematical technique is employed to automatically process the data set (S) in a manner that comprises the following steps:

Defining a Point Spread Function (PSF) (K) that, for each value of n, has a kernel value $K_n$ representing the behavior of the probing beam in a bulk of the sample for beam parameter value $P_n$;

Defining a spatial variable (V) that represents a physical property (O) of the sample as a function of position in its bulk;

Defining an imaging quantity (Q) that, for each value of n, has a value $Q_n$ that is a three-dimensional convolution of $K_n$ and V, such that $Q_n = K_n * V$;

For each value of n, computationally determining a minimum divergence $$\min D(M_n \| K_n * V)$$

between $M_n$ and $Q_n$, wherein one solves for V while applying constraints on the values $K_n$.

The invention exploits a number of insights that allowed the above-mentioned mathematical approach to be developed. In particular, the inventor realized that:

Signals associated with stimulated radiation in a sample—such as BS electrons, secondary electrons and X-rays—generally yield sufficient information from all generation depths within their detectable range.

The PSF of stimulated radiation in several types of samples, including stained bio-samples and polymers, is generally (highly) linear.

In complex samples, encountered across a range of applications, signals coming from levels located at different depths in a sample tend to be highly independent in a statistical sense, given that different layers are likely to contain different structures and a wide range of local density and topology variations.

With these insights in mind, one can elucidate the current inventive approach as follows.

The formation of an image I (e.g. a BS image) in a linear sample can be described as a three-dimensional (3D) convolution of a PSF K and a spatial variable V representing some physical property (O) of the sample as a function of position in its bulk (e.g. staining concentration), i.e.:

I can be described as K*V.

If a beam parameter (P) of the probing beam changes, the 3D shape of K will also generally change. For example, if the primary beam landing energy increases, the PSF will extend significantly in the z direction, but also in x/y directions if the employed landing energies are sufficiently high. For a component image In out of a measurement series n=[1, . . . , N] obtained at different landing energies En, component image formation is such that:

In can be described as Kn*V.

The inventive deconvolution process consists of computationally recovering the various kernels $K_n$ along with the unknown spatial variable V. This can be done by minimizing a divergence (distance) D between the estimated unknown variables and the observed image sequence:

$$\min D(I_n \| K_n * V).$$

If one assumes no knowledge about either the sample or the PSF kernels, one obtains a 3D blind deconvolution task. On the other hand, if one can apply constraints on the variables $K_n$ (e.g. pursuant to simulations, empirical measurements, etc.—see below), then one need only optimize for the spatial variable V, resulting in the following simultaneous optimization tasks:

$$\min D \ (I_1 \| K_1 * V),$$
$$\vdots$$
$$\min D \ (I_N \| K_N * V),$$

which can be solved for V.

In the dissertation above (and also below), it should be explicitly noted that:

The measured stimulated radiation need not comprise BS electrons: one can also exploit other types of stimulated radiation, such as secondary electrons or X-ray radiation, for example.

The varied beam parameter (P) need not be landing energy (beam energy): instead, one can choose to vary beam parameters such as beam convergence angle (incidence angle) or beam focal depth (penetration depth), for example. It should also noted that, when varying P, one may choose to vary it in constant increments ΔP, or variable increments, or a mixture of both.

The image I referred to cannot be directly observed—it must instead be indirectly divined from measurements of a specific measurand M. This measurand M might, for example, be detector current (e.g. when detecting electrons as stimulated radiation) or intensity (e.g. when detecting X-rays as stimulated radiation), etc.

The physical property O alluded to need not be staining agent concentration—it could also be a property such as atomic density or secondary emission coefficient, for example.

In general, the method according to the invention does not (directly) result in an absolute determination of the property O as a function of position within the bulk of the sample. Instead, it allows determination of the local values of the spatial variable V associated with O, e.g. the relative variations in O throughout the sample.

The charged-particle probing beam need not be an electron beam: it could also be an ion beam, for example. In this respect, the skilled artisan will appreciate that, when an ion beam (e.g. a beam of Gallium or Helium ions) interacts with a sample, it will also generally produce stimulated radiation as discussed above.

There is a difference between the spatial dimensionality of something (such as a PSF or a convolution) and the number of variables that it comprises. For example, a PSF that is spatially three-dimensional can be a function of (many) more than three variables. It is also important to note that such variables might be vectors and or scalars, for example.

The "constraints" applied on the values Kn during the de-convolution process are applied ex post facto rather than ab initio. In other words, the values $K_n$ going into the convolution $Q_n = K_n * V$ are generic, and attempted simplification is only applied during the ensuing de-convolution. To better understand this difference, one can make an analogy to a problem in which a product of two functions is integrated. In such a situation, the generic problem:

$$\int_a^b U(x)V(x)\,dx$$

is generally not the same as the specific problem:

$$(U(b) - U(a))\int_a^b V(x)\,dx$$

In an embodiment of the method according to the present invention, said constraints on the values $K_n$ are derived using at least one method selected from the group comprising:

(i) Computational simulation of at least a set of values $K_n$;
(ii) Empirical determination of at least a set of values $K_n$;
(iii) Modeling of the Point Spread Function (K) as a parameterized function with a limited number of model parameters, on the basis of which at least a set of values $K_n$ can be estimated;
(iv) Logical solution space limitation, whereby theoretically possible values $K_n$ that are judged to be physically meaningless are discarded;
(v) Inference of a second set of values $K_n$ by applying extrapolation and/or interpolation to a first set of values $K_n$.

These various methods can be elucidated in more detail as follows:

In (i), mathematical techniques are used to emulate the behavior of charged particles and photons in materials, allowing the form of the PSF to be calculated and representative values $K_n$ to be predicted. The accuracy and extent of the simulation outcome will depend inter alia on the computational/computer resources dedicated to the task in question. Examples of mathematical simulation techniques suitable for this purpose are Monte Carlo methods, Finite Element Analysis, etc. For more information on such techniques, see, for example:

http://en.wikipedia.org/wiki/Monte_Carlo_method
http://en.wikipedia.org/wiki/Finite_element_method In (ii), use is made of observations of the actual behavior of charged particles and photons in given materials. Such observations may, for example, be the outcome of actual imaging sessions performed on other samples, or of specific experiments performed on homogeneous material samples, etc. For example, when employing the current invention to image a semiconductor sample comprising a portion of a silicon wafer on which various patterned metallic and dielectric layers have been deposited, one might derive a collection of $K_n$-values from one or more of the following:

Other imaging sessions performed on similar semiconductor samples;

Specific "calibration tests" performed on blank silicon wafers;

Investigative experiments performed using various test coatings on silicon wafers, etc.

In (iii), one attempts to intuitively estimate what mathematical form a PSF might have, and then construct a parameterized model on this basis, using a limited number of relatively straightforward model parameters. A similar approach is used to construct, for example, climate change models, or behavioral models of crowds. By definition, the outcome of such a model will be a simplification, but it will allow a good general grasp of the basic conduct of the system being investigated.

In (iv), one seeks to intuitively limit the size of a possible solution space by "weeding out" results that are theoretically possible but that are adjudged to be devoid of physical reality. For example, one might constrain the PSF to yield only positive values, or restrict it to a differential (i.e. smoothly varying) functional form, or place limits on its statistical dependence, etc.

In (v), having obtained a first set of $K_n$-values $\{K_n\}_1$, a second set of $K_n$-values $\{K_n\}_2$ is derived therefrom on the basis of extrapolation and/or interpolation. For example, if the elements of $\{K_n\}_1$ are observed to lie on a smooth, monotonic curve, one can use interpolation to infer the positions of intermediate elements and/or extrapolation to infer the positions of boundary elements of the set.

In another embodiment of a method according to the present invention, said minimum divergence is selected from the group comprising Least Squares Distance, Csiszar-Morimoto F-divergences, Bregman Divergences, Alpha-Beta-Divergences, the Bhattacharyya Distance, the Cramér-Rao Bound, derivatives of these, and combinations hereof. The particular choice of the type of divergence will depend inter alia on the statistical nature of the assumed noise in the computation in question. For example, in the particular case of Gaussian noise, one could elect to minimize the Least Squares distance (also called the Mean Squares distance):

$$\min \|M_n - K_n * V\|^2,$$

whereas, for other noise models, one could use one of the other divergence measures referred to above. With regard to these broad divergence classes, the following can be noted:

Csiszar-Morimoto F-divergences (and derived measures) include the I and J Kullback-Leibler divergences, the Total Variation, Harmonic Mean, and Chi-Square measures, as well as several other entropy-based measures. See, for example:

http://en.wikipedia.org/wiki/F-divergence.

Bregman Divergences (and derived measures) include inter alia the Mahalonobis distance. See, for example:

http://en.wikipedia.org/wiki/Bregman_divergence

Alpha-Beta-Divergences (and derived measures) include measures such as the generalized Kullback-Leibler, Triangular Discrimination, and Arithmetic Geometric measures. See, for example:

Cichocki, A; Cruces, S; Amari, S., *Generalized Alpha-Beta Divergences and Their Application to Robust Nonnegative Matrix Factorization*, Entropy 13, 134-170 (2011).

Cichocki, A; Amari, S, *Families of Alpha-Beta-and Gamma-Divergences: Flexible and Robust Measures of Similarities*, Entropy, 12, 1532-1568 (2010).

The Bhattacharyya Distance measures the similarity of two discrete or continuous probability distributions. See, for example:

http://en.wikipedia.org/wiki/Bhaitacharyya_distance

For additional information, see, for example:

http://en.wikipedia.org/wiki/Least_squares http://en.wikipedia.org/wiki/Kullback-Leibler_divergence http://en.wikipedia.org/wiki/Cramer-Rao_bound The actual minimization (i.e. optimization) of the chosen divergence can be performed using a variety of techniques, such as Gradient-Descent methods, Stochastic methods, and Expectation-Maximization Maximum Likelihood and Maximum À Priori methods, for example. Iterative techniques which use derivatives, among which the Gradient Descent method, Conjugate Gradient method, Newton's method, the Quasi-Newton method, the Levenberg-Marquardt method, and Interior Point methods are some of the most commonly used; the convergence of such methods can be ensured by employing Line-Searches and Trust-Region methods, for example. As an alternative to gradient-based iterative techniques, one can employ optimization heuristics that impose fewer or no constraints on the functions to be optimized. Such heuristic methods search for solutions by relying mostly on stochastic strategies. Examples include Simulated Annealing, Evolutionary Algorithms, the Tabu Search, and Particle Swarm Optimization. Other popular heuristics include the Nelder-Mead Simplex and Hill Climbing algorithms, for example. For more information on such minimization techniques, see reference [4] quoted in Embodiment 2 below, and also refer to the following sources:

http://en.wikipedia.org/wiki/Mathematical_optimization http://en.wikipedia.org/wiki/Expectation-maximization_algorithm The methodology set forth above can be described as entailing "computational slicing" into a sample. It is advantageous in that it provides very good z-resolution, but is limited as regards the extent of its z-penetration into the sample. If desired, such computational slicing can be combined with "physical slicing", so as to provide a hybrid approach that augments the obtainable z-penetration. Such physical slicing involves the physical removal of (at least one layer of) material from the sample, and may, for example, be performed using mechanical techniques (e.g. using a microtome/diamond knife) and/or radiative/ablative techniques (e.g. using a laser beam or broad ion beam, or milling the sample by scanning a focused ion beam over it) and/or etching techniques (such as beam-induced etching, chemical etching or reactive etching, for example). It should be noted that, in the case of such physical slicing, the employed layer removal procedure need not be destructive: instead, there are (mechanical) techniques that allow a removed layer to be preserved and (re-)imaged at a later juncture, if desired.

In a particular embodiment of such a hybrid computational/physical slicing approach, the above-mentioned computational slicing and physical slicing are employed alternately, whereby:

An exposed surface S of a sample is investigated using the computational slicing technique according to the current invention;

A physical slicing technique is then used to "skim" off material from the surface S, thus creating a newly exposed surface S' at a depth d below S;

This newly exposed surface S' is then investigated using the computational slicing approach according to the current invention;

If desired, several iterations of this hybrid approach can be performed, involving alternate application of computational slicing and physical slicing, and thus providing greater and greater z-penetration into the sample.

It should be noted that, in its broadest form, the three-dimensional deconvolution technique provided by the current invention allows full 3D deconvolution of accrued data. However, in simplified approaches, the invention may, for example, also be used to perform quasi-three-dimensional (so-called 2.5D) deconvolution. For example, one could conceive a measurement situation where the PSF is essentially (quasi-)planar in form, e.g. because of beam shaping and/or a certain layered/partitioned geometry of the sample being investigated; in such a scenario, one could conceive a 2D deconvolution. Building upon this example, if data were accrued during a scanning motion conducted essentially perpendicular to said (quasi-)planar PSF, the intrinsic 2D nature of the original measurement scenario can be made quasi-3D (i.e. 2.5D), because the scanning motion allows (limited) additional information to be gleaned in a third dimension. In any event, both such three-dimensional scenarios (full 3D, 2.5D) are fundamentally different to the (quasi-)1D scenario addressed in the above-mentioned document EP-A 11163992.

One should take care not to confuse the present invention—which provides a form of (hybrid) computational tomography in SEM—with existing "classical" tomographic techniques based on Transmission Electron Microscopy (TEM), in which depth information is gleaned from a sample by employing a range of different sample tilt angles. Inter alia, one can identify the following differences between the two:

By its very nature, TEM tomography does not generate the type of convoluted depth data associated with the present invention, and, accordingly, does not require statistical processing techniques to perform depth resolution upon such convoluted data. In this regard, one should note that, in TEM, a probing electron beam gets transmitted all the way through a sample, without generating the stimulated radiation intrinsic to SEM.

The TEM approach uses much higher input beam energies (typically of the order of 200-300 keV), which can cause sample damage. In contrast, the method according to the present invention works satisfactorily with much lower input beam energies (e.g. of the order of 1-5 keV).

TEM tomography can only be used on very thin samples (generally<1 μm in thickness). Because the present invention does not rely on transmission of electrons through the sample, it does not suffer from this restriction on sample thickness.

A SEM-based technique such as that used in the present invention has a much greater lateral reach than a TEM-based technique, because of the (lateral) scanning nature of the former (although this difference is alleviated to some extent when one uses a Scanning TEM (STEM) instead of a conventional TEM).

TEM apparatus is generally much more expensive than SEM apparatus.

Care should be taken not to confuse the very broad and general methodology of the current invention with the much more restricted techniques set forth in various prior-art publications. In this respect, it is important to explicitly note that:

The approach of the current invention does not place any ab initio restrictions on the form/nature of the employed PSF; it instead allows a completely general, spatially three-dimensional PSF to start off with.

The approach of the current invention does not place any ab initio restrictions on the substance/nature/structure of the material in the sample being investigated; it instead permits a completely general bulk sample to be assumed.

The present invention places no ab initio restrictions on the type/geometry of radiation used to perform the various measurement sessions.

The current invention performs a series of different measurement sessions at different beam parameters, thereby accruing a convoluted mass of data from different (three-dimensional) positions within a sample. This mass of data is then subjected to full three-dimensional deconvolution so as to "un-mix" the data mass into individually resolved contributions from distinct voxels within the sample. In this way, volume re-construction of the sample is achieved, thus revealing details from different depths (z) and from different lateral positions (x, y).

The inventive deconvolution procedure iterates over all PSFs during said re-construction process. In this regard, the PSFs are deconvolved in a coupled/concurrent fashion rather than in an independent fashion. Such coupling tends to enhance convergence to a good solution set. To better understand the difference between coupled/concurrent and uncoupled/separated deconvolution, one can make an analogy to a problem in which simultaneous equations are solved. If the equations are indeed solved simultaneously (i.e. in a coupled manner), then all variables in the equations remain "floating" during the solving process. On the other hand, if the equations are tackled one-at-a-time (i.e. in an uncoupled manner), then all variables except one will have to be "pinned" during the solving process for each individual equation, leading to a much more restricted solution set.

To highlight these aspects of the current invention, the following distinctions can be pointed out:

(a) In US 2011/0187847 A1, use is made of so-called "degradation functions" that are 2D in nature rather than 3D, and that are recovered separately (for each measurement modality) rather than concurrently. Data thus recovered are combined using convex weighting factors, thus performing re-convolution rather than de-convolution. This document accordingly does not (and cannot) achieve computational depth slicing into the employed sample; instead, its aim is to improve lateral resolution only.

(b) The journal article by Giuseppe Pezzotti et al. in J. Appl. Phys. 104 (2), July 2008, pp 23514 et seq. concentrates on a highly simplified analysis in which:

The very specific sample studied is assumed to be highly homogeneous, with well-known stress fields characterized by relatively simple models having limited numbers of parameters. Such a simple à priori analytic model is at variance with the general samples dealt with in the current invention.

So-called "Probe Response Functions" are employed, which are constants that are completely determined prior to fitting/deconvolution, using experimental calibrations applied to (constant) test cross-sections of the sample. Such an approach could not be applied in the case of a general sample, in which cross-sections would be mutually different.

The "deconvolution" performed is very limited in nature, amounting to no more than a very confined scalar fit. It pales compared to the full variable voxel recovery performed by the current invention.

(c) The journal article by Zhu Wenliang et al. in J. Appl. Phys. 101(10), May 2007, pp 103531 et seq. does not attempt to recover subsurface information at all. Instead, it uses a fully known 2D PSF to restore lateral stress profiles in a specific sample structure.

(d) The journal article by V. Kh. Alimov et al. in J. Nucl. Mater. 337-339, March 2005, pp 619-623 describes a procedure that is totally different to the current invention. Instead of varying a beam parameter and performing several measurement sessions, this journal article instead uses the very specific SIMNRA model fitting technique to remove degeneracy from a single ion beam spectrum. This relies on a detailed advance model of the scattering behavior of ions in the sample in question (e.g. taking into account factors such as the mass of the probing ions, their energy loss as a function of penetration, etc.) to perform an iterative fit to the obtained spectrum, and thus distill the concentration of a specific element (deuterium) present at various subsurface levels in the sample.

These comparisons serve to highlight how broad the approach of the current invention is, to accentuate its full 3D nature, and to emphasize its applicability to completely generic samples.

DETAILED DESCRIPTION OF THE DRAWINGS

The invention will now be elucidated in more detail on the basis of exemplary embodiments and the accompanying schematic drawings, in which.

Figure 5:
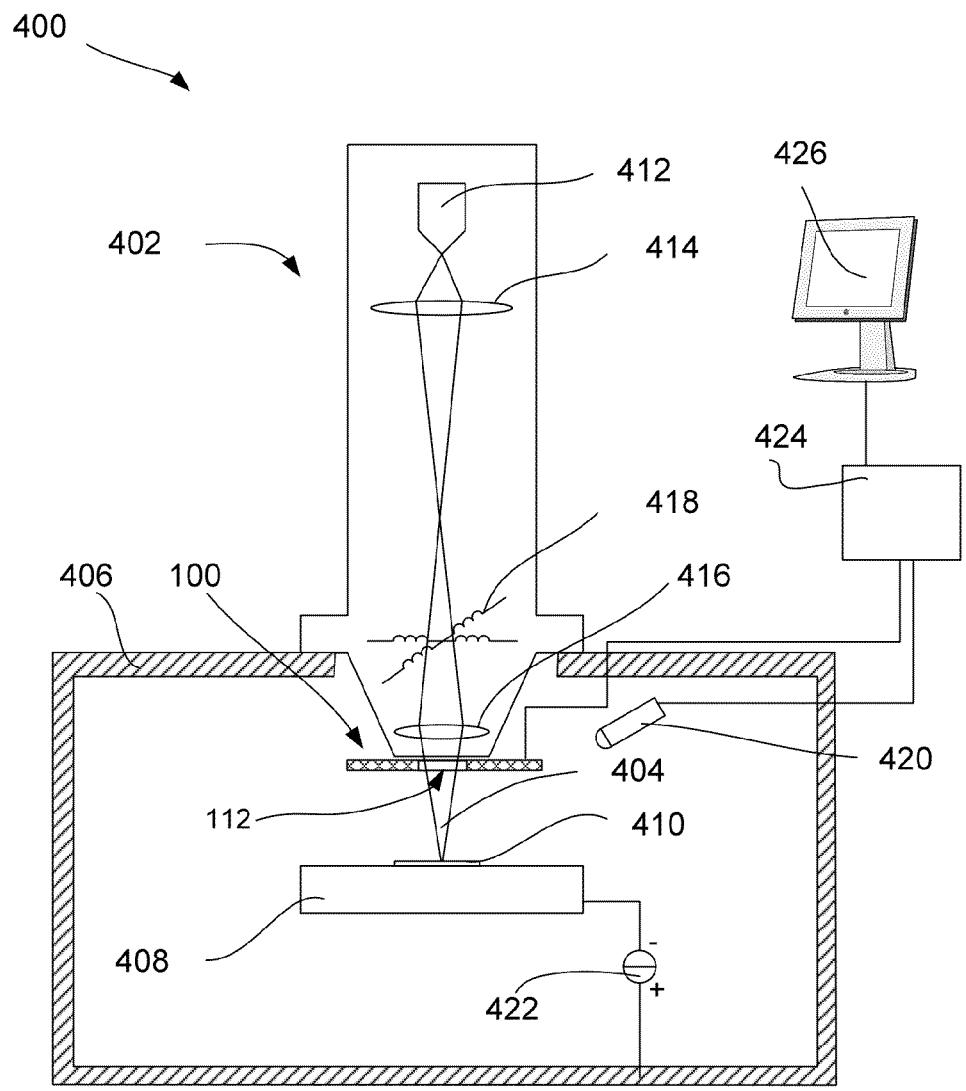

FIG. 5 renders a longitudinal cross-sectional view of aspects of a particle-optical microscope (in this case a SEM) with which the method according to the current invention can be implemented.

In the Figures, where pertinent, corresponding parts are indicated using corresponding reference symbols.

EMBODIMENT 1

Figure 1:
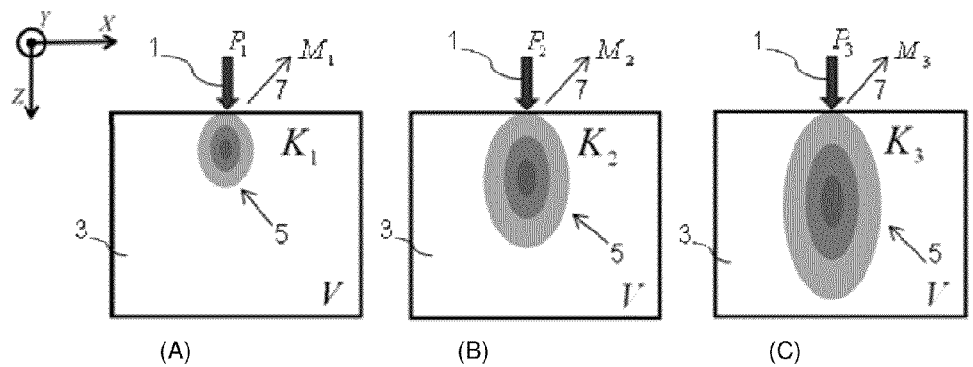
FIG. 1 depicts part of a measurement sequence attendant to an embodiment of a method according to the current invention.

FIG. 1 schematically depicts part of a measurement sequence comprised in an embodiment of a method according to the current invention. The figure has three sub-figures, (A)-(C), respectively representing three successive measurement sessions in a sequence [1, ..., N]. A general member of the sequence [1, ..., N] is denoted by the integer n.

Each sub-figure renders a cross-sectional view of an interaction between an incoming probing beam of radiation 1 and a portion of a sample 3 being investigated. The beam 1 propagates in a z direction but, when it strikes the sample 3, it produces a three-dimensional interaction region 5 within the sample 3, with a longitudinal component in z and with lateral components in x and y. Progressing from sub-figure (A) to (C), a parameter P of the beam 1 has had its value changed between measurement sessions, e.g. having distinct values $P_1$, $P_2$ and $P_3$ for the three sub-figures, respectively. This parameter P may, for example, be the landing energy of the beam 1.

Associated with the interaction region 5 of the beam 1 with the sample 3 is a Point Spread Function (PSF) K, with a kernel value that changes in reaction to changes in P; in this particular case, as landing energy is increased, the PSF swells in size. Accordingly, PSF kernel values $K_1$, $K_2$ and $K_3$ are associated with the beam parameter values $P_1$, $P_2$ and $P_3$, respectively.

The interaction of the beam 1 with the sample 3 produces stimulated radiation 7, which originates from the interaction region 5 and is generally emitted from the surface of the sample 3 facing the incoming beam 1. In the current schematic depiction, this stimulated radiation 7 is denoted using a single arrow, so as not to clutter the figure; however, in reality, such stimulated radiation 7 will be emitted in a whole range of directions. Examples of such stimulated radiation are BS electrons, secondary electrons and X-rays. Using one or more detectors (not depicted in FIG. 1; see FIG. 5, for example), the stimulated radiation 7 can be detected. A measurand M (e.g. detector current or intensity) is associated with such detection, allowing the stimulated radiation 7 to be quantified. In this way, measurand values $M_1$, $M_2$ and $M_3$ are obtained, corresponding to the PSF kernel values $K_1$, $K_2$ and $K_3$, respectively.

The sample 3 has a physical property O that influences the sample's interaction with the incoming beam 1; for example, O might be the atomic density or secondary emission coefficient of the sample. In the current scenario, one would like to find out something about a functional form of O at different positions (x, y, z) within the sample 3, e.g. the relative variation in O from point to point. This functional form is represented here by a spatial variable V. Distilling information about V will generally yield important insights into the internal structure and nature of the sample 3.

When one measures the stimulated radiation 7 via the measurand M, one is actually observing a convoluted "tangle" of information concurrently coming from various different points within the interaction region 5. Because this information is convoluted in this way, it does not directly yield the desired point-to-point information about V. However, the current invention addresses this problem, by providing a computational technique by which said information can be deconvoluted (i.e. "disentangled" or spatially resolved).

To this end, the invention defines an imaging quantity (Q) that, for each value of integer n in the measurement sequence [1, ..., N], has a value $Q_n$ that is a three-dimensional convolution of $K_n$ and V, i.e. $Q_n = K_n * V$. For each value of n, one then computationally determines a minimum divergence D between $M_n$ and $Q_n$, i.e. one optimizes:

$$\min D(M_n \| K_n * V).$$

Figure 2A:
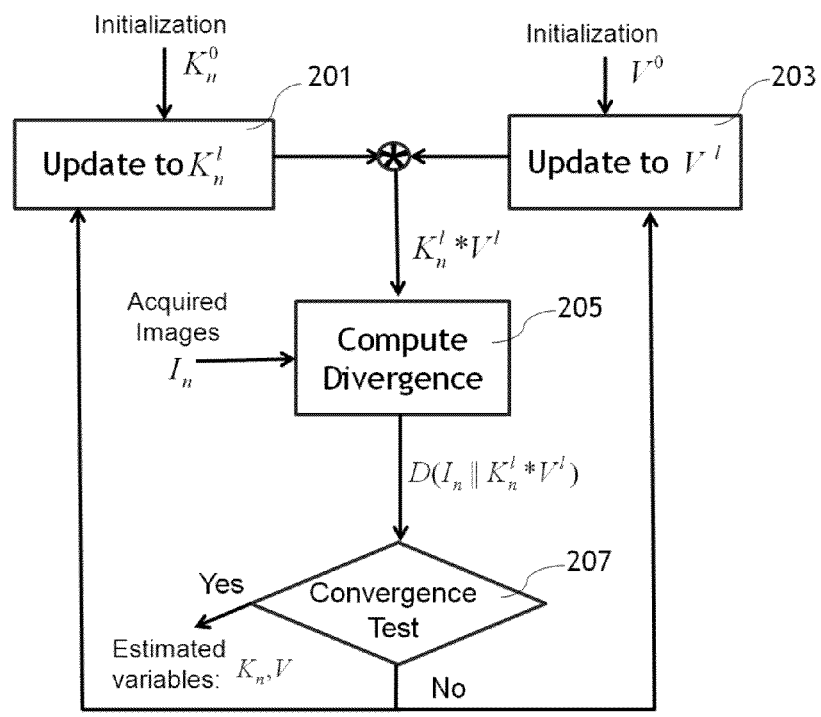
FIGS. 2A and 2B are mutually associated flowcharts that depict a general scheme for performing the method according to the present invention.
Figure 2B:
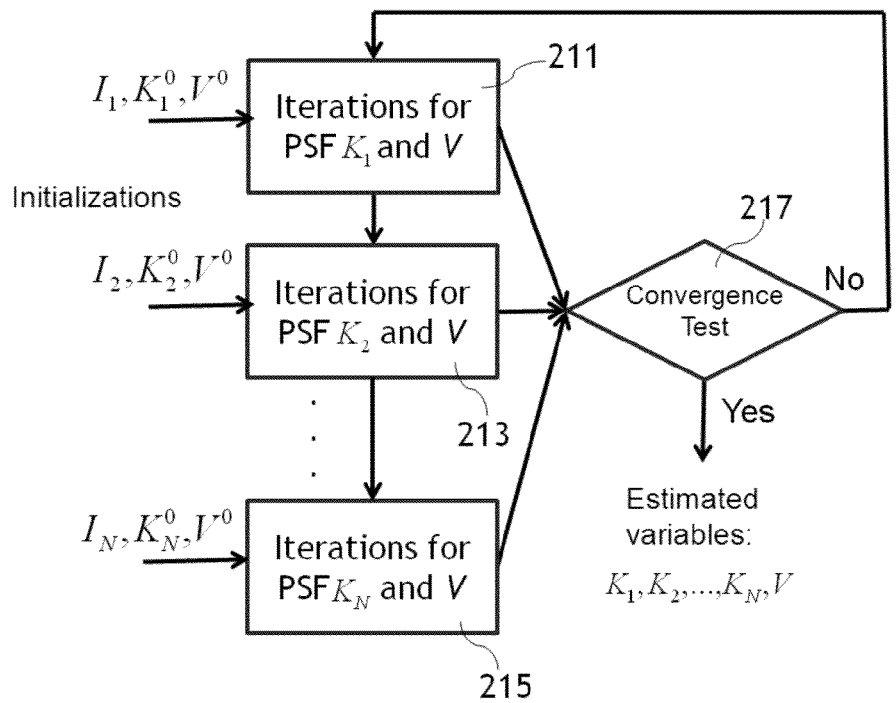

This problem can be solved for V by applying appropriate constraints on the values $K_n$. This approach is schematically illustrated in the flowcharts of FIGS. 2A and 2B, wherein it should be noted that:

FIG. 2A depicts an algorithm for a given PSF kernel $K_n$ at iteration 1. Multiple iteration cycles for a given $K_n$ are applied sequentially.

The iterative scheme in FIG. 2A needs to be sequentially applied to each PSF and to the spatial variable V. For any pair $K_n$,V, one can have one or more iterations at each cycle.

In said flowcharts, the indicated steps will now be elucidated in more detail. Starting with FIG. 2A:

201: This step represents the value of $K_n$ at iteration l (i.e. $K_n^l$). In the special case l=1, a preceding initialization procedure will have been performed, so as to "kick start" the iteration procedure.

203: Similarly, this step represents the value of V at iteration 1 (i.e. $V^l$). Once again, in the special case l=1, a preceding "kick start" initialization procedure will have been performed.

205: The convolution $K_n^l * V^l$ is calculated using the output of steps 201 and 203. One now introduces a quantity $I_n$ that is a dimensionless/scaled version of the quantity $M_n$. For example, if $M_n$ is measured in volts, its numerical value in volts is dimensionless, and can, if desired, be scaled by the value of the fundamental electron charge (e) so as to effect a conversion to a numerical value in electron-volts (eV), for example. This is purely a matter of choice in any given situation, as will be readily grasped by the skilled artisan. The quantity $I_n$ will be referred to hereinafter as an "image". In step 205, a divergence between image $I_n$ and the convolution $K_n^l * V^l$ is determined, i.e. $D(I_n \| K_n^l * V^l)$ is calculated.

207: Here, it is determined if the divergence calculated in step 205 is minimal, i.e. if convergence has been attained. If it is ("Yes"), then one has distilled the sought values $K_n$ and V; if it is not ("No"), then one returns to the top of the flowchart for the next iteration (l+1). Turning now to FIG. 2B, this figure represents a generalization of FIG. 2A. Instead of just showing the procedure for only one element n of the measurement sequence [1, ..., N], it now depicts all the elements 1 ... N in this sequence:

211, 213, 215: Each of these steps corresponds to the cumulative steps 201, 203 and 205 of FIG. 2A, but now shown for the individual cases n=1 (211), n=2 (213) and n=N (215).

217: This step corresponds to step 207 of FIG. 2A.

For a specific example as to how the minimum divergence problem set forth above can be formulated and solved, reference is made to the next Embodiment below.

EMBODIMENT 2

One intuitive way to consider the variable-kernel deconvolution task at hand is to formulate it using so-called Bayesian statistics.

One first defines a number of probabilities that will be used throughout the elucidation below:

$Pr(V|I_n)$ is the probability of distilling the spatial variable V, given the acquired input values $I_n$ (see the above discussion of step 205 in the flowchart of FIG. 2A for an explanation of the concept of "image" value $I_n$).

$Pr(V)$ is the prior probability associated with V, representing one's knowledge about the structure to be reconstructed.

$Pr(I_n)$ is the probability associated with the acquired images; however, this is essentially a constant, given that the images $I_n$ are actually observed/measured values.

Using Bayes' rule one now obtains:

$$Pr(V|I_n) = \frac{Pr(I_n|V)Pr(V)}{Pr(I_n)} \quad (1)$$

In the Bayesian framework, the current problem can be expressed as the following maximization task:

$$\hat{V} = \mathrm{argmax}_{V \geq 0}\{Pr(V|I_n)\}, \quad (2)$$

in which one needs to enforce the positivity of the reconstructed variable V. This is necessary in order to obtain a physically meaningful solution. More commonly, one will use the so called log-likelihood function to simplify the calculations:

$$\hat{V} = \mathrm{argmin}_{V \geq 0}\{-\log(Pr(V|I_n))\} \quad (3)$$

Concretely, the current imaging process is well represented by a Poisson process. Given the nature of charged-particle and X-ray detectors, one can assume that, at each voxel x in a 3D grid $\Omega$, the image is formed by the realization of independent Poisson processes. This leads to:

$$Pr(V|I_n) = \Pi_{x \in \Omega} \frac{((K_n * V)(x))^{I_n(x)} \exp(-(K_n * V)(x))}{I_n(x)!}, \quad (4)$$

wherein it should be noted that "x" is not the linear Cartesian coordinate x, but is instead an algebraic denotation of a three-dimensional position.

To recover the volume V, one needs to minimize the criterion:

$$I((V|I_n)) = -\log(Pr(V|I_n)) \quad (5)$$
$$= \Sigma_{x \in \Omega}((K_n * V)(x)) - I_n(x).\log((K_n * V)(x)) + \log(I_n(x)!)$$

Given that the $\Sigma_{x \in \Omega} \log(I_n(x)!)$ term does not contain any variables, the criterion can be redefined as:

$$J((V|I_n)) = \Sigma_{x \in \Omega}((K_n * V)(x)) - I_n(x).\log((K_n * V)(x)) \quad (6)$$

It is important to note that this criterion is related to Kullback-Leibler generalized I-divergence $IDIV(I_n \| V)$. This can be seen from the definition of I-divergence:

$$IDIV(I_n \| V) \stackrel{def}{=} \Sigma_{x \in \Omega} I_n(x) \log\left(\frac{I_n(x)}{(K_n * V)(x)}\right) - \Sigma_{x \in \Omega} I_n(x) - (K_n * V)(x)) \quad (7)$$

from which one can obtain:

$$IDIV(I_n \| V) = J((V|I_n)) - \Sigma_{x \in \Omega} I_n(x).\log(I_n(x)) \quad (8)$$

The second term in (8) is a constant with regard to minimization and, hence, minimizing $J((V|I_n))$ is equivalent to minimizing $IDIV(I_n|V)$.

Reference is now made to the following journal article:

[1] H. Lantéri, M. Roche, C. Aime, *"Penalized maximum likelihood image restoration with positivity constraints: multiplicative algorithms, Inverse Problems,"* vol. 18, pp. 1397-1419, 2002, in which it was shown that a positivity-constrained minimization problem of the type (2) above can be solved using the following iterative scheme:

$$V^{l+1}(x) = V^l(x) \cdot \left(\frac{I_n(x)}{(K_n * V^l)(x)} * K_n(-x)\right) \quad (9)$$

This algorithm is also known as the Maximum-Likelihood Expectation Maximization algorithm, which is further described, for example, in the following references:

[2] L. Shepp, Y. Vardi, *"Maximum-Likelihood reconstruction for emission tomography,"* IEEE Transactions on Medical Imaging, MI-5, pp. 16-22, 1982.

[3] Richardson, William Hadley. *"Bayesian-Based Iterative Method of Image Restoration"*, JOSA 62 (1), pp 55-59, 1972.

Convergence in expression (9) can be accelerated by using the exponent q as follows:

$$V^{l+1}(x) = V^l(x) \cdot \left(\frac{I_n(x)}{(K_n * V^l)(x)} * K_n(-x)\right)^q \quad (10)$$

Typically, $q \in [1, 1.5]$ and, in addition to acceleration, it can act as a regularizing factor. In the current case, the iterative algorithm needs to be sequentially used for all kernels $K_n$ associated with the different PSFs. Convergence can be assessed empirically or based on other criteria, such as the relative change in the variables.

If one needs to recover or adjust the values of the PSF kernels $K_n$, one can use alternate minimization of the spatial variable V and the $K_n$ variables. One then obtains the following algorithm:

$$V^{l+1}(x) = V^l(x) \cdot \left(\frac{I_n(x)}{(K_n^l * V^l)(x)} * K_n^l(-x)\right)^q \quad (11)$$

$$K_n^{l+1}(x) = K_n^l(x) \cdot \left(\frac{I_n(x)}{(K_n^l * V^{l+n})(x)} * V^{l+1}(-x)\right)^q$$

One can choose to have more iterations for the kernels $K_n$ or for the spatial variable V at each cycle; such a choice can be determined based on experience/experimentation. For example, it is generally noticed that V tends to converge faster, and hence more iterations can be spent searching for the different values $K_n$.

If prior knowledge about the PSF or V is available, it can be incorporated into the Bayesian formulation using a combination of conditional Pr(.|.) and joint probabilities Pr(.,.) as follows:

$$Pr(V, K_n | I_n) = \frac{Pr(I_n | V \cdot K_n) Pr(V) Pr(K_n)}{Pr(I_n)} \quad (12)$$

It follows that the minimization problem (2) is then modified as follows:

$$\hat{V} = \mathrm{argmax}_{V \geq 0} \{Pr(V, K_n | I_n)\} \quad (13)$$

and the log-likelihood criterion to be minimized then becomes $$J(V, K_n | I_n) = -\log(Pr(I_n | V, K_n)) - \log(Pr(V)) - \log(Pr(K_n)) \quad (14)$$

$$= J(I_n | V, K_n) + J(V) + J(K_n)$$

While the first term is the data term that ensures that one fits the observations, the second and third terms are known as regularization terms that use one's knowledge and assumptions about the variables to limit the space of solutions and reduce the effects of noise. The criterion $J(V, K_n | I_n)$ can be minimized using the Maximum Likelihood Expectation Maximization approach. Optimization can be also carried using a variety of other convex and non-convex methods, as set forth, for example, in the following reference:

[4] William H. Press, Saul A. Teukolsky, William T. Vetterling, Brian P. Flannery, *Numerical Recipes in C: The Art of Scientific Computing*, Second Edition (1992).

For completeness, it is noted that the approach set out in the current Embodiment can be regarded as a hybrid/variant of the so-called Richardson-Lucey Algorithm (RLA). The RLA is a known mathematical technique that can be applied to solve a variety of problems. For example, it was used by NASA scientists in an attempt to computationally improve blurred imagery from the original (i.e. uncorrected) Hubble Space Telescope.

EMBODIMENT 3

Figure 3:
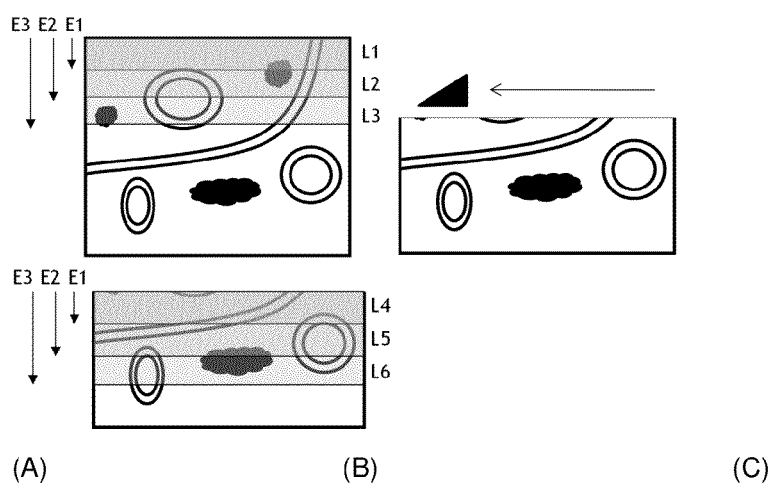
FIG. 3 illustrates a hybrid technique involving the alternate use of computational slicing and physical slicing as set forth above.

FIG. 3 illustrates an embodiment of the current invention whereby computational slicing is combined with physical slicing, so as to allow charged-particle-microscopy-based 3D volume imaging of a sample.

FIG. 3A (left) depicts a computational slicing step, whereby a sample is scanned at varying landing energies ($E_1$, $E_2$, $E_3$) and a 3D deconvolution algorithm is applied, as set forth above. This allows sub-surface virtual imaging of the sample to increasing penetration depths, here schematically labeled as ($L_1$, $L_2$, $L_3$).

In FIG. 3B (center), subsequent use is made of a physical slicing step, whereby a mechanical cutting device (e.g. a diamond knife) or a non-mechanical approach (e.g. involving a focused/broad beam of ions, or a focused electromagnetic beam) is used to physically "skim off" a certain depth of material from the sample, thus producing a newly exposed surface.

In FIG. 3C (right), one executes a subsequent computational slicing operation on said newly exposed surface. This allows sub-surface virtual imaging of the sample to new penetration depths, here schematically labeled as ($L_4$, $L_5$, $L_6$).

Figure 4:
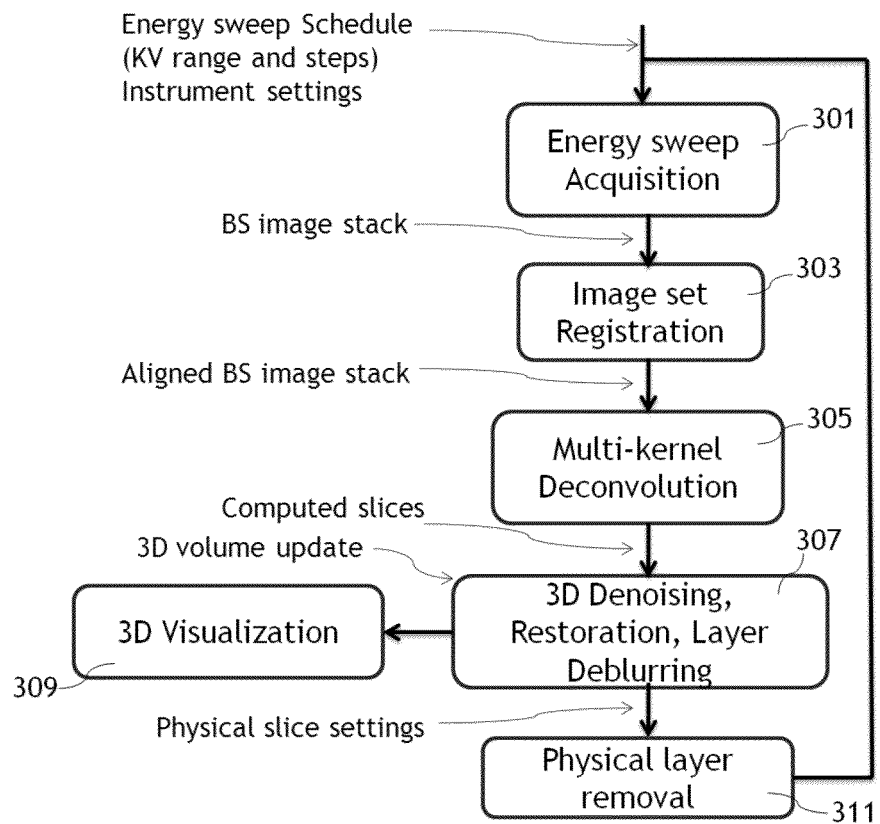
FIG. 4 is a flowchart that illustrates the alternate application of computational slicing and physical slicing in one or more iterations.

This combined/hybrid approach is further elucidated in the flowchart of FIG. 4. The computational slicing procedure (301-309) in this flowchart is similar to that described above, but is here followed by a physical slicing procedure (311), with a subsequent (iterative) return to the top of the flowchart. Such alternate application of computational slicing and physical slicing techniques can be repeated for as many iterations as are necessary to achieve a given cumulative z-penetration into a particular sample.

In the flowchart of FIG. 4, the indicated steps will now be elucidated in more detail:

301: This acquisition step involves:
Irradiating a sample using a charged-particle beam in a plurality (N) of measurement sessions, each measurement session having a different beam parameter (P).
Detecting, via a measurand (M), stimulated radiation emitted by the sample during each measurement session, thus compiling a data set $\{P_n, M_n\}$, where n is an integer in the range $1 \leq n \leq N$.

In the current case, P is landing energy, the stimulated radiation comprises BS electrons, and M is the detected BS current. Step 301 is preceded by preparatory considerations in which it is decided inter alia what energies will be used in the acquisition step.

303: The BS image stack, i.e. the data set $\{P_n, M_n\}$, can, if required, undergo a (slight) distortion correction, to correct for "drift effects" (e.g. thermally induced imaging/measurement fluctuations) in the measuring apparatus between the various measurement sessions in step 301. Such distortion correction may involve operations such as data scaling, shifting, rotating, skewing, etc. In this manner, a so-called "aligned" image stack is obtained.

305: In this step, a 3D deconvolution step as set forth above is performed on the aligned data set.

307: As a finishing touch, the outcome of step 305 can (optionally) be subjected to various "polishing up" procedures, such as de-noising, de-blurring, etc.

309: The data resulting from step 305 (and, if relevant, the follow-up step 307) now yield the desired 3D sub-surface visualization of the sample concerned.

311: It one wants to computationally visualize a sub-surface region of the sample that is more deeply located than can be reached by a single "iteration" of steps 301-309, then a combined computational and physical slicing approach can be employed. To this end, in step 311, a layer of material is physically removed from the exposed surface of the sample, and one then returns to the top of the flowchart for a new "iteration" of steps 301-309.

EMBODIMENT 4

FIG. 5 shows a charged-particle microscope 400, which, in this case, is a SEM. The microscope 400 comprises a particle-optical column 402, which produces a charged-particle beam 404 (in this case, an electron beam). The particle-optical column 402 is mounted on a vacuum chamber 406, which comprises a sample holder/stage 408 for holding a sample 410. The vacuum chamber 406 is evacuated using vacuum pumps (not depicted). With the aid of voltage source 422, the sample holder 408, or at least the sample 410, may be biased (floated) to an electrical potential with respect to ground.

The particle-optical column 402 comprises an electron source 412, lenses 414, 416 to focus the electron beam 404 onto the sample 410, and a deflection unit 418. As regards detectors, the apparatus is equipped with:

A first detector 420, for detecting a first type of stimulated emitted radiation emanating from the sample 410 in response to irradiation by the beam 404. In the present example, the detector 420 is an X-ray detector (such as an EDS or WDS detector) for detecting X-rays.

A second detector 100, for detecting a second type of stimulated radiation emitted from the sample 410 in response to irradiation by the beam 404. In the present example, the detector 100 is a segmented electron detector.

As here depicted, the apparatus uses both of these detector types; however, this is purely a design/implementation choice and, if desired, it's also possible to use just one of these detectors types. The apparatus further comprises a computer processing apparatus (controller) 424 for controlling inter alia the deflection unit 418, lenses 414, and detectors 420, 100, and displaying information gathered from the detectors 420,100 on a display unit 426.

By scanning the beam 404 over the sample 410, stimulated radiation—comprising, for example, X-rays, secondary electrons (SEs) and backscattered electrons (BEs)—emanates from the sample 410. X-rays are detected by first detector 420, whereas SEs/BEs are detected by second detector 100. As the emitted radiation is position-sensitive (due to said scanning motion), the information obtained from the detectors 420, 100, will also be position-dependent.

The signals from the detectors 420,100 are processed by the processing apparatus 424, and displayed on display unit 426. Such processing may include operations such as combining, integrating, subtracting, false colouring, edge enhancing, and other processing known to the person skilled in the art. In addition, automated recognition processes, e.g. as used for particle analysis, may be included in such processing.

In the context of the current invention:

The measurand M is associated with the output of detector 420 and/or 100;

The beam parameter P is varied by adjusting the particle source 412 and/or the particle-optical column 402 and/or the biasing voltage source 422 so as to change a characteristic of the beam 404, such as the landing energy of its constituent particles on the sample 410. Using different values $P_n$ of P (for measurement sessions n in the sequence [1, . . . , N]) one obtains associated values $M_n$ of M, allowing a dataset $\{P_n, M_n\}$ to be accrued.

The processing apparatus 424, or a dedicated separate processing unit (not shown), is used to perform the various mathematical manipulations on the data set $\{P_n, M_n\}$ prescribed by the current invention (as set forth above).

By way of example, which is not intended to be in any way limiting upon the scope of the invention but is merely presented here for the purpose of illustrating a concrete, practical situation:

The varied parameter P is landing energy, and it is adjusted in constant increments of $\Delta P=50$ eV. Other values may, of course, be chosen, depending inter alia on the desired resolution. In practice, landing energy values in the range 500 eV-7 keV, for example, are found to be useful.

N=25, i.e. 25 different values of $P_n$ are employed. Other values may, of course, be chosen, depending inter alia on the desired computational penetration into the sample.

The cumulative virtual penetration into a typical biological sample is of the order of about 50-75 nm. This may seem small, but it nevertheless allows investigators to glean a great quantity of sub-surface information from a typical sample. For example, a so-called lipid bilayer membrane in a biological sample has a thickness of only about 2-3 nm, so it can easily be computationally imaged using the inventive approach.

It should be noted that many refinements and alternatives of such a set-up will be known to the skilled artisan, including, but not limited to, the detection of (infrared/visible/ultraviolet) light emanating from the sample 410, the use of dual beams (for example an electron beam 404 for imaging and an ion beam for machining (or, in some cases, imaging) the sample 410), the use of a controlled environment at the sample 410 (for example, maintaining a pressure of several mbar—as used in a so-called Environmental SEM—or by admitting gasses, such as etching or precursor gasses), etc.

We claim as follows:

1. A method of investigating a sample using charged-particle microscopy, comprising:

irradiating a surface of the sample using a probing beam of charged particles in a plurality (N) of measurement sessions, each measurement session having an associated beam parameter (P) value that is chosen from a range of such values and that differs between measurement sessions; and detecting stimulated radiation emitted by the sample during each measurement session, associating a measurand (M) therewith and noting the value of this measurand for each measurement session, thus allowing compilation of a data set (S) of data pairs $\{P_n, M_n\}$, where n is an integer in the range $1 \leq n \leq N$, in which a mathematical technique is employed to automatically process the data set (S) in a manner that comprises:

defining a Point Spread Function (K) that, for each value of n, has a kernel value $K_n$ representing the behavior of the probing beam in a bulk of the sample for beam parameter value $P_n$;

defining a spatial variable (V) that represents a physical property (O) of the sample as a function of position in its bulk;

defining an imaging quantity (Q) that, for each value of n, has a value $Q_n$ that is a three-dimensional convolution of $K_n$ and V, such that $Q_n=K_n*V$;

for each value of n, computationally determining a minimum divergence $$minD(M_n\|K_n*V)$$

between $M_n$ and $Q_n$, wherein one solves for V while applying constraints on the values $K_n$.

2. The method according to claim 1, wherein said constraints on the values $K_n$ are derived using at least one method selected from the group comprising:

computational simulation of at least a set of values $K_n$;

empirical determination of at least a set of values $K_n$;

modeling of the Point Spread Function (K) as a parameterized function with a limited number of model parameters, on the basis of which at least a set of values $K_n$ can be estimated;

logical solution space limitation, whereby theoretically possible values $K_n$ that are judged to be physically meaningless are discarded; and inference of a second set of values $K_n$ by applying extrapolation and/or interpolation to a first set of values $K_n$.

3. The method according to claim 2, wherein said computational simulation is performed with the aid of a technique selected from the group comprising Monte Carlo simulation, Finite Element Analysis, and combinations hereof.

4. The method as claimed in claim 1, wherein said minimum divergence is selected from the group comprising Least Squares Distance, Csiszar-Morimoto F-divergences, Bregman Divergences, Alpha-Beta-Divergences, the Bhattacharyya Distance, the Cramér-Rao Bound, derivatives of these, and combinations hereof.

5. The method as claimed in claim 1, wherein:

the beam parameter (P) is selected from the group comprising beam energy, beam convergence angle and beam focal depth;

the stimulated radiation is selected from the group comprising secondary electrons, backscattered electrons and X-ray radiation;

the measurand (M) is selected from the group comprising intensity and current.

6. The method according to claim 1, wherein said physical property (O) of the sample is selected from the group comprising staining agent concentration, atomic density, and secondary emission coefficient.

7. The method according to claim 1, wherein:

said steps of irradiating the surface of the sample, detecting stimulated radiation emitted by the sample to obtain the data set (S), and computing the spatial variable (V) are comprised in a computational slicing step;

said computational slicing step is combined with a physical slicing step, whereby a physical material removal method is used to physically remove a layer of material from the original surface of the sample, thereby revealing a newly exposed surface of the sample.

8. The method as claimed in claim 7, wherein said physical material removal method is selected from the group comprising mechanical slicing with a blade device, ion milling with an ion beam, ablation with a beam of electromagnetic energy, beam-induced etching, chemical etching, reactive etching, and combinations hereof.

9. The method as claimed in claim 7, wherein said computational slicing step and said physical slicing step are alternately repeated in multiple iterations.

10. An apparatus constructed and arranged to carry out a method as claimed in claim 1.

11. The apparatus of claim 10 comprising:

a particle optical column which produces a charged particle beam, the particle optical column comprising an electron source, lenses, and a deflection unit;

a vacuum chamber, said particle optical column is mounted on the vacuum chamber, the vacuum chamber comprises a sample holder or stage;

at least one vacuum pump to evacuate the vacuum chamber;

at least one detector to detect the stimulated radiation; and a voltage source for biasing the sample holder or stage, or at least the sample, to an electrical potential with respect to the ground.

12. The apparatus of claim 11 in which the at least one detector comprises:

a first detector for detecting a first type of stimulated radiation emanating from the sample in response to irradiation by the beam; and a second detector for detecting a second type of stimulated radiation emitted from the sample in response to irradiation by the beam.

13. The apparatus of claim 12 in which the first detector and the second detector comprise X-ray detectors or segmented electron detectors.

14. The apparatus of claim 11 further comprising:

a computer processing apparatus for controlling the deflection unit, lenses, and the at least one detector and comprise signal processing operations; and a display unit for displaying information gathered from the at least one detector.

15. The apparatus of claim 14 in which the signal processing operations comprise combining, integrating, subtracting, false colouring, edge enhancing, or automated recognition processes used for particle analysis.

16. The apparatus of claim 14 in which:

the measurand M is associated with the output of the at least one detector;

the beam parameter P is varied by adjusting the source of the particle optical column, particle optical column, and/or the biasing voltage source; and the computer processing apparatus performs the various mathematical manipulations on the data set $\{P_n, M_n\}$ prescribed by the current invention.

17. The apparatus of claim 11 comprising an electron beam for imaging and ion beam for machining or imaging.

18. The method as claimed in claim 1, wherein said stimulated radiation emitted by a sample comprises backscattered electrons, secondary electrons, x-rays, infrared light, visible light, or ultraviolet light.

19. The method of claim 1 in which irradiating the surface of the sample comprises a beam energy less than 200 keV.

20. The method of claim 1 in which irradiating the surface of the sample comprises a beam energy of 1-5 keV.

* * * * *